United States Patent [19] [11] 4,223,035
Bastian [45] Sep. 16, 1980

[54] TREATING PROSTATE HYPERTROPHY WITH 4-(4H-BENZO[4,5]CYCLOHEPTA[1,2-B]THIOPHEN-4-YLIDENE)-1-METHYL-PIPERIDINES

[75] Inventor: Jean-Michel Bastian, Therwil, Switzerland

[73] Assignee: Sandoz Ltd., Basel, Switzerland

[21] Appl. No.: 927,540

[22] Filed: Jul. 24, 1978

Related U.S. Application Data

[63] Continuation of Ser. No. 768,716, Feb. 15, 1977, abandoned, which is a continuation-in-part of Ser. No. 602,121, Aug. 5, 1975, abandoned, which is a continuation-in-part of Ser. No. 511,627, Oct. 3, 1974, abandoned.

[30] Foreign Application Priority Data

Oct. 8, 1973 [CH] Switzerland .................. 14308/73

[51] Int. Cl.² .................. A61K 31/445; C07D 409/08
[52] U.S. Cl. .................... 424/267; 260/961; 546/202; 549/44; 549/74; 549/79
[58] Field of Search ............... 260/332.3 P; 424/267; 546/202

[56] References Cited

U.S. PATENT DOCUMENTS 3,491,103  1/1970  Jucker et al. ............... 546/202
3,682,930  8/1972  Bourquin et al. ............ 546/202
4,024,266  5/1977  Bastian .................... 546/202

Primary Examiner—Henry R. Jiles
Assistant Examiner—Richard A. Schwartz
Attorney, Agent, or Firm—Gerald D. Sharkin; Robert S. Honor; Thomas O. McGovern

[57] ABSTRACT

This invention provides new compounds of formula I,

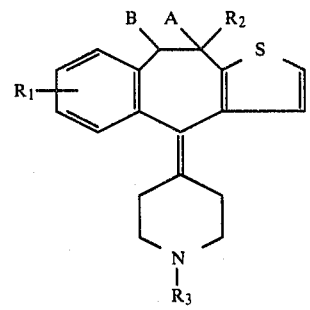

wherein
  $R_1$ is hydrogen, chlorine or lower alkyl,
  $R_2$ is lower alkyl,
  $R_3$ is lower alkyl, each of
  A and B is hydrogen, or
  A and B together form a bond,
useful as luteinizing hormone secretion inhibitors, e.g. for the treatment of prostate hypertorphy.

5 Claims, No Drawings

TREATING PROSTATE HYPERTROPHY WITH 4-(4H-BENZO[4,5]CYCLOHEPTA[1,2-B]THIOPHEN-4-YLIDENE)-1-METHYLPIPERIDINES

This is a continuation of application Ser. No. 768,716 filed Feb. 15, 1977, now abandoned which in turn is a continuation-in-part of Ser. No. 602,121, filed Aug. 5, 1975, now abandoned, which in turn is a continuation-in-part of Ser. No. 511,627, filed Oct. 3, 1974, now abandoned.

The present invention relates to new heterocyclic compounds.

In accordance with the invention there are provided new compounds of formula I,

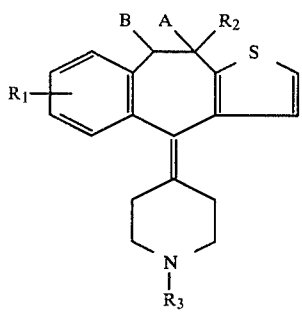

wherein $R_1$ is hydrogen, chlorine or lower alkyl,
$R_2$ is lower alkyl,
$R_3$ is lower alkyl, each of
A and B is hydrogen, or
A and B together form a bond.

Further, in accordance with the invention a compound of formula I may be obtained by a process comprising removing water from a compound of formula II,

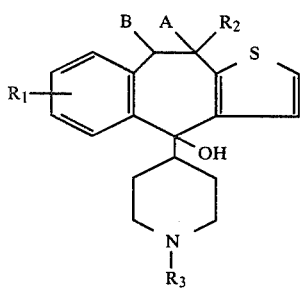

wherein $R_1$, $R_2$, $R_3$, A and B are as defined above.

$R_1$ in the compounds of formula I preferably signifies hydrogen. Any substituents $R_1$ which may be present preferably are in the 6 or 7 position of the ring structure. When $R_1$ is lower alkyl, this preferably contains 1 to 3 carbon atoms and especially signifies methyl. The lower alkyl group represented by the symbol $R_2$ preferably contains 1 to 4 carbon atoms and especially signifies the methyl group. The lower alkyl group represented by the symbol $R_3$ preferably contains 1 to 4 carbon atoms and especially signifies the methyl group. A and B preferably signify hydrogen. The preferred compounds are those wherein $R_1$ is hydrogen, $R_2$ is methyl, each of A and B is hydrogen, and $R_3$ is lower alkyl, preferably methyl.

Any carbon containing radical not particularly defined herein preferably has up to 5 carbon atoms.

The process of the invention for the removal of water from compounds of formula II may be effected in a manner known for analogous carbinols, e.g. by the action of suitable water-removing agents on the compounds of formula II. Examples of water-removing agents which may be used are mineral acids or strong organic acids, e.g. hydrogen chloride, trifluoroacetic acid, benzenesulphonic acid, or acid anhydrides or acid halides, e.g. acetic anhydride or thionyl chloride. An inert organic solvent may be present. For example hydrogen chloride may be used in the form of an alcoholic solution thereof, e.g. with isopropanol, or admixed with glacial acetic acid. The removal of water is preferably effected at a temperature between about 0° and 100° C.

The compounds of formula I may be isolated from the reaction mixture and purified in known manner. Free base forms may be converted into acid addition salt forms in conventional manner and vice versa. Suitable inorganic acids include hydrochloric acid. Suitable organic acids include malonic acid, maleic acid and fumaric acid.

The starting materials may, for example, be obtained as follows:

(a) A compound of formula II may, for example, be obtained by condensing a compound of formula III,

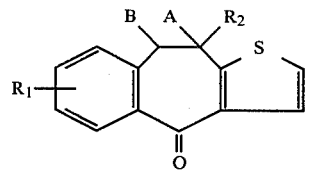

wherein $R_1$, $R_2$, A and B are as defined above, with an organometallic compound of formula X,

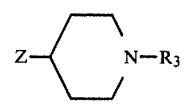

wherein $R_3$ is as defined above, and
Z is lithium, or a halogen magnesium radical —MgX$^I$, wherein X$^I$ is chlorine, bromine or iodine.

The process may, for example, be effected in an organic solvent suitable for Grignard reactions, e.g. an ether such as diethyl ether or tetrahydrofuran, and optionally an aromatic hydrocarbon such as benzene. The temperature may be between −20 and 80° C., preferably between 20° and 50° C. The hydrolysis of the organometallic complex formed as intermediary may be effected in known manner, e.g. with an aqueous ammonium chloride solution.

(b) A compound of formula IIIa,

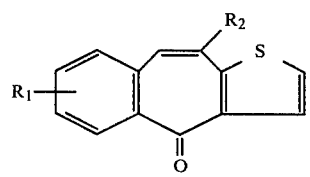

wherein $R_1$ and $R_2$ are as defined above, may for example, be obtained removing hydrogen bromide from a compound of formula IV,

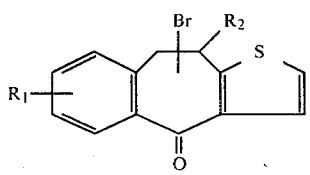

wherein $R_1$ and $R_2$ are as defined above, and the bromine atom is in a 9 or 10 position, obtainable by brominating a compound of formula IIIb,

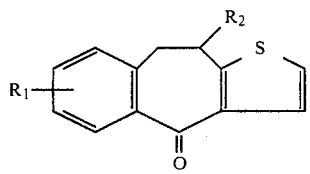

wherein $R_1$ and $R_2$ are as defined above.

The bromination of a compound of formula IIIb may, for example, be effected by reaction with the calculated amount of a brominating agent, e.g. n-bromosuccinimide. A peroxide, e.g. benzoyl peroxide is preferably present as catalyst. Suitable solvents are preferably halogenated hydrocarbons, e.g. carbon tetrachloride. The reaction temperature preferably is between about 20° C. and the boiling temperature of the reaction mixture. The removal of hydrogen bromide from a compound of formula IV may be effected under alkaline reaction conditions. This may, for example, be effected with an organic base, e.g. triethylamine or pyridine or an inorganic base.

The temperature may be between about 0° and 100° C. Examples of suitable solvents are chlorinated hydrocarbons, acetone, or aromatic hydrocarbons such as benzene or toluene.

(c) A compound of formula IIIb may, for example, be obtained by cyclizing a compound of formula V,

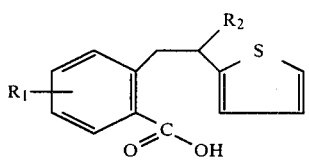

wherein $R_1$ and $R_2$ are as defined above. The cyclization of a compound of formula V is preferably effected in the presence of a strong acid catalyst, e.g. a strong mineral acid, preferably polyphosphoric acid or sulphuric acid. An inert organic solvent, e.g. a hydrocarbon such as toluene or xylene is preferably present. The reaction temperature preferably is between 50° and 160° C., and the reaction time may be from 5 minutes to 10 hours. In place of an acid of formula V it is also possible to use, for example, a reactive derivative of such an acid for the cyclization. Examples of suitable reactive derivatives are acid halides or acid anhydrides or lower alkyl esters of an acid of formula V. In accordance with a process variant an acid of formula V may, for example, first be converted into an acid chloride thereof with an inorganic acid chloride, e.g. thionyl chloride. This acid chloride may subsequently be cyclized under the reaction conditions of a Friedel-Crafts reaction in the presence of a Friedel-Crafts catalyst, such as aluminium chloride, in an inert organic solvent.

(d) A compound of formula V may, for example, be obtained by reduction of a compound of formula VI,

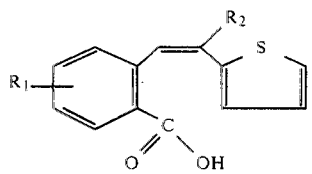

wherein $R_1$ and $R_2$ are as defined above. The reduction of a compound of formula VI may, for example, be effected with nascent hydrogen, e.g. by treating the compound of formula VI with sodium amalgam/alcohol. The reduction may alternatively be effected by catalytic hydrogenation. The catalytic hydrogenation may, for example, be effected in the presence of a solid catalyst, preferably a palladium catalyst, in known manner in an inert organic solvent, e.g. dimethyl formamide or a lower alcohol, at a temperature between preferably 30° and 100° C., at 5 to 100 atmospheres of hydrogen pressure, or by passing hydrogen through the reaction mixture. An organic phosphine rhodium complex may, for example, also be used as catalyst for the dehydrogenation. Thus, for example, a compound of formula VI may be hydrogenated using tris-(triphenylphosphine)rhodium chloride as catalyst in an alcoholic solution, at a hydrogen pressure of approximately 1 to 6 atmospheres and a reaction temperature of about 40° to 60° C.

(e) A compound of formula VI may, for example, be obtained by hydrolyzing a compound of formula VII,

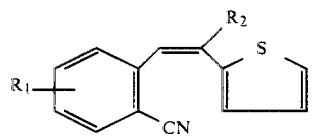

wherein $R_1$ and $R_2$ are as defined above. The hydrolysis is preferably effected in an alkaline medium, e.g. with potassium or sodium hydroxide, in a high boiling alcohol, e.g. methylisobutylcarbinol or n-butanol or a high boiling ether, e.g. diethylene glycol monomethylether, preferably at the boiling temperature of the reaction mixture, e.g. 160° C.

(f) A compound of formula VII may, for example, be obtained by condensing a dialkyl-(o-cyanobenzyl)phosphonate of formula VIII,

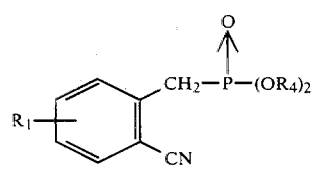

wherein $R_1$ is as defined above, and
$R_4$ is lower alkyl,
with an alkyl-2-thiophene-ketone of formula IX,

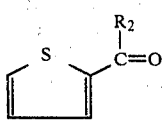

wherein R₂ is as defined above. The reaction may, for example, be effected under the reaction conditions of a Wittig reaction modified in accordance with Horner, in an inert organic solvent, in the presence of a strong basic condensation agent. Dimethyl formamide, optionally diluted with a lower alcohol or ether, e.g. 1,2-dimethoxyethane, is preferably used as solvent. An alkali metal alcoholate or hydride, e.g. sodium ethylate, methylate or hydride or potassium tert.butylate, is preferably used as basic condensation agent. The reaction temperature may be between 20° and 150° C.

(g) A compound of formula V may be alternatively obtained by hydrolysing a compound of formula X,

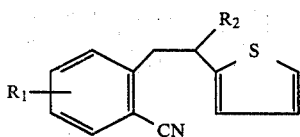

wherein R₁ and R₂ are as defined above, e.g. under reaction conditions as described under process variant (e) above (h) A compound of formula X may be for example obtained by reduction of a compound of formula VII, e.g. under the catalytic reduction conditions as described under process variant (d) above.

Insofar as the production of the starting materials is not described, these are known or may be produced in accordance with known processes, or in a manner analogous to the processes described herein or to known procesees.

In the following non-limitative Examples all temperatures are indicated in degrees Centigrade.

EXAMPLE 1

4-(9,10-dihydro-10-methyl-4H-benzo[4,5]-cyclohepta[1,2-b]thiophen-4-ylidene)-1-methylpiperidine A solution of 17.0 g of 9,10-dihydro-10-methyl-4-(1-methyl-4-piperidyl)-4H-benzo[4,5]cyclohepta[1,2-b]thiophen-4-ol in 350 cc of isopropanol and 350 cc of a 7 N solution of hydrogen chloride in isopropanol is heated to the boil for 4 hours, is evaporated to dryness, the residue is taken up in 150 cc of water, is made alkaline with concentrated caustic soda solution and extracted with methylene chloride. The extracts are washed with water, dried over potassium carbonate, decolourized with animal charcoal and concentrated by evaporation. The title compound, obtained as oily residue, is converted into the hydrochloride form in ethanol. M.P. of the hydrochloride form of the title compound: decomp. from 210° (from acetone/ethanol). M.P. (hydrogen malonate 191°-2° C.)

The starting material may be produced as follows: (a) A solution of 10.0 g of 2-acetylthiophene and 21.0 g of diethyl-o-cyanobenzylphosphonate in 70 cc of anhydrous dimethyl formamide is added dropwise at 20°-30° in an atmosphere of nitrogen to a suspension of 4.5 g of pulverized sodium methylate in 100 cc of anhydrous dimethyl formamide, the reaction mixture is stirred at 40° for 2 hours, and at 100° for a further 2 hours, is cooled to room temperature and diluted with 600 cc of ice water. The condensation product is extracted with ether, the extract is washed with water until neutral, is dried over potassium carbonate and concentrated by evaporation. The evaporation residue is chromatographed through 110 g of silica gel with a mixture of benzene/petroleum ether (1:4). The 2-[2-(2-thienyl)-1-propenyl]benzonitrile ($n_D^{20}=1.6460$, B.P. 165°-175°/0.1 mm Hg), isolated as main fraction, is used for the next reaction without further purification.

(b) A solution of 14.0 g of the product obtained above in 400 cc of ethanol is hydrogenated in the presence of 4.0 g of 5% palladium on aluminium oxide at 100° and 21 atmospheres for 24 hours. After filtering over diatomaceous earth, the solution is evaporated to dryness, and the 2-[2-(2-thienyl)propyl]-benzonitrile, obtained as oily residue, is used for the next reaction without special purification.

(c) 12.0 g of the product obtained above are slowly added at 100° to a mixture of 24.0 g of potassium hydroxide in 60 cc of diethylene glycol monomethyl ether. The reaction mixture is stirred at 160° for 6 hours, is cooled to about 70° and poured on 300 cc of hot water. After cooling, the resulting solution is washed with toluene, acidified with concentrated hydrochloric acid and extracted with ether. The ethereal extracts are washed with water, dried over magnesium sulphate and concentrated by evaporation. The 2-[2-(2-thienyl)-propyl]benzoic acid, obtained as residue, is crystallized from hexane. M.P. 66°-68°.

(d) A mixture of 10.0 g of the acid obtained above and 100 g of polyphosphoric acid is heated to 130° for 45 minutes, is cooled to 90° and poured on 500 cc of water. The resulting solution is extracted with methylene chloride, the organic solution is washed with a dilute sodium carbonate solution and water, dried over sodium sulphate and concentrated by evaporation. The evaporation residue is distilled in a high vacuum, whereby 9,10-dihydro-10-methyl-4H-benzo[4,5]cyclohepta[1,2-b]thiophen-4-one distils at 160°-165°/0.1 mm Hg. M.P. 67°-68° (from ether).

(e) 4.8 g of iodine-activated magnesium are covered with a layer of 60 cc of anhydrous tetrahydrofuran and cauterized with a few drops of ethylene bromide. A solution of 25.0 g of 4-chloro-1-methylpiperidine in 160 cc of anhydrous tetrahydrofuran is then added dropwise at such a rate that the solvent boils continually, and stirring is subsequently effected at the boil for 2 hours. The reaction mixture is cooled to 10°, and a solution of 20.0 g of 9,10-dihydro-10-methyl-4H-benzo[4,5]cyclohepta-[1,2-b]thiophen-4-one in 100 cc of anhydrous tetrahydrofuran is added dropwise at this temperature. After stirring at room temperature for 1½ hours and at the boil for 30 minutes, the reaction mixture is cooled, poured on 300 cc of a 20% ammonium chloride solution, and the organic phase is separated. The aqueous solution is extracted with methylene chloride, the combined organic solutions are washed with water, dried over sodium sulphate and concentrated by evaporation. The 9,10-dihydro-10-methyl-4-(1-methyl-4-piperidyl)-4H-benzo[4,5]cyclohepta-[1,2-b]thiophen-4-ol, obtained as residue, is recrystallized twice from isopropanol. M.P. 177°-178°.

EXAMPLE 2

4-(10-ethyl-9,10-dihydro-4H-benzo[4,5]-cyclohepta[1,2-b]thiophen-4-ylidene)-1-methylpiperidine A solution of 15.0 g of 10-ethyl-9,10-dihydro-4-(1-methyl-4-piperidyl)-4H-benzo[4,5]cyclohepta-[1,2-b]thiophen-4-ol in 450 cc of a 3.5 N solution of hydrogen chloride in isopropanol is heated to the boil for 4 hours, and the title compound obtained after working up the reaction mixture is converted into the hydrogen fumarate form thereof. M.P. 220°–221° (from methanol/ethanol).

Starting material:

(a) 2-[2-(2-thienyl)-1-butenyl]benzonitrile, purification of the crude product by distillation, B.P. 150°–153°/0.2 mm Hg;

(b) 2-[2-(2-thienyl)butyl]benzonitrile, purified by distillation, B.P. 128°–132°/0.1 mm Hg;

(c) 2-[2-(2-thienyl)butyl]benzoic acid, used for the next reaction in crude state;

(d) 10-ethyl-9,10-dihydro-4H-benzo[4,5]cyclohepta-[1,2-b]thiophen-4-one, purified by distillation, B.P. 185°–190°/0.1–0.15 mm Hg;

(e) 10-ethyl-9,10-dihydro-4-(1-methyl-4-piperidiyl)-4H-benzo[4,5]cyclohepta[1,2-b]thiophen-4-ol, produced from 2.4 g of magnesium, 12.5 g of 4-chloro-1-methylpiperidine and 10 g of 10-ethyl-9,10-dihydro-4H-benzo[4,5-cyclohepta[1,2-b]thiophen-4-one in 150 cc of tetrahydrofuran. M.P. 145°–148° (from isopropanol).

EXAMPLE 3

4-(10-methyl-4H-benzo[4,5]cyclohepta[1,2-b]-thiophen-4-ylidene)-1-methylpiperidine The title compound is produced in a manner analogous to that described in Example 1, from 1.0 g of 10-methyl-4-(1-methyl-4-piperidyl)-4H-benzo[4,5]-cyclohepta[1,2-b]thiophen-4-ol in 40 cc of a 3.5 N solution of hydrogen chloride in isopropanol. M.P. of the hydrochloride form: decomp. from 295°.

The starting material may be produced as follows:

(a) A mixture of 20.0 g of 9,10-dihydro-10-methyl-4H-benzo[4,5]cyclohepta[1,2-b]thiophen-4-one, 15.6 g of N-bromosuccinimide and 0.5 g of dibenzoyl peroxide in 150 cc of anhydrous carbon tetrachloride is slowly heated to 70°, whereby an exothermic reaction develops, and heating to the boil is subsequently effected for 2 hours. After cooling, the precipitated succinimide is filtered off, the filtrate is evaporated to dryness and the residue is heated to the boil in 130 cc of triethylamine for 2 hours. The solvent is removed by evaporation, the residue is dissolved in methylene chloride and water, the organic phase is separated and washed with 2 N hydrochloric acid and then with water. After removing the solvent by evaporation, the residue is distilled in a high vacuum, whereby 10-methyl-4H-benzo[4,5]-cyclohepta[1,2-b]thiophen-4-one distils at 205°–210°/0.1 mm Hg. M.P. 75°–76° (from ether).

(b) 10-methyl-4-(1-methyl-4-piperidyl)-4H-benzo[4,5]-cyclohepta[1,2-b]thiophen-4-ol, produced from 1.2 g of magnesium, 6.8 g of 4-chloro-1-methylpiperidine and 5.4 g of 10-methyl-4H-benzo[4,5]-cyclohepta[1,2-b]thiophen-4-one in 50 cc of anhydrous tetrahydrofuran, used for the next reaction in crude state.

The following 10-alkyl-4-(1-alkyl-4-piperidylidene)-4H-benzo[4,5]cyclohepta[1,2-b]thiophene derivatives may also be obtained in a manner analogous to that described in Example 1, by removal of water from the corresponding 10-alkyl-4-(1-alkyl-4-piperidyl)-4H-benzo[4,5]cyclohepta[1,2-b]thiophen-4-ol derivatives:

| Ex.Nr. | Compound | Remarks, physical constants |
|---|---|---|
| 4 | 4-(10-ethyl-9,10-dihydro-4H-benzo[4,5]cyclohepta[1,2-b]thiophen-4-ylidene)-1-ethylpiperidine | M.P. of the hydrogen malate 154°–156° (from ethanol) |
| 5 | 4-(9,10-dihydro-10-methyl-4H-benzo[4,5]cyclohepta[1,2-b]thiophen-4-ylidene)-1-ethylpiperidine | M.P. of the hydrogen malate 162°–164° (from ethanol) |
| 6 | 4-(7-chloro-9,10-dihydro-10-methyl-4H-benzo[4,5]cyclohepta[1,2-b]thiophen-4-ylidene)-1-methylpiperidine | |
| 7 | 4-(9,10-dihydro-6,10-dimethyl-4H-benzo[4,5]cyclohepta[1,2-b]thiophen-4-ylidene)-1-ethylpiperidine | |
| 8 | 4-(7-chloro-10-methyl-4H-benzo[4,5]cyclohepta[1,2-b]thiophen-4-ylidene)-1-ethylpiperidine | |
| 9 | 4-(10-n-butyl-9,10-dihydro-4H-benzo[4,5]cyclohepta[1,2-b]thiophen-4-ylidene)-1-methylpiperidine | |
| 10 | 4-(9,10-dihydro-10-n-propyl-4H-benzo[4,5]cyclohepta[1,2-b]thiophen-4-ylidene)-1-methylpiperidine | |
| 11 | 4-(9,10-dihydro-10-methyl-4H-benzo[4,5]cyclohepta[1,2-b]thiophen-4-ylidene)-1-n-buylpiperidine | |
| 12 | 4-(9,10-Dihydro-10-methyl-4H-benzo[4,5]cyclohepta[1,2-b]thiophen-4-ylidene)-1-n-propylpiperidine | M.P. 115–117° |

The compounds of formula I are useful as luteinizing hormone secretion inhibitors, e.g. for the treatment of prostate hypertrophy, as indicated by an inhibition of luteinizing hormone secretion shown in standard tests, e.g. in adult female rats on s.c. and p.o. administration of about 0.05 to about 0.5 mg/kg animal body weight of the compounds of noon of the proestrus day whereupon both an inhibition of the expected increase in the level of luteinizing hormone in the blood serum and an inhibition of the expected ovulation during the following night, is observed.

For this use the dosage will, of course, vary depending on the compound employed, mode of administration and treatment desired. However, in general, satisfactory results are obtained when administered at a daily dosage of from about 0.01 mg to about 50 mg/kg animal body weight, conveniently given in divided doses 2 to 4 times a day or in sustained release form. For the larger mammals, the total daily dosage is in the range from about 0.5 to about 100 mg, and dosages forms suitable for oral administration comprise from about 0.1 mg to about 50 mg of the compounds admixed with a solid or liquid pharmaceutical carrier or diluent.

Additionally, the compounds of formula I are useful as anti-depressant agents, as indicated by standard tests, e.g. on i.p. administration of from about 0.05 to about 40 mg/kg animal body weight of the compounds by an inhibition of tetrabenazine-induced catalpsy in rats.

For the above mentioned use the dosage will, of course, vary depending on the compound employed, mode of administration and therapy desired. However, in general, satisfactory results are obtained when administered at a daily dosage of from 0.05 mg to about 40 mg per kg animal body weight, conveniently given in divided doses 2 to 4 times a day or in sustained release form. For the larger mammal, the total daily dosage is in the range from about 3 to about 150 mg, and dosage forms suitable for oral administration comprise from about 0.7 mg to about 75 mg of the compounds admixed with a solid or liquid pharmaceutical carrier or diluent.

The compounds are also useful as anti-cholinergic agents for the treatment of, for example, Parkinson's disease as indicated by antagonism of tremors caused by Oxotremorin in mice at a dosage of, for example, 1 to 4 mg/kg body weight; and block arecoline arousal in rabbits at a dosage of, for example, 0.05 to 0.4 mg/kg body weight.

For this use, the dosage will, of course, vary depending on the compound employed, mode of administration and therapy required. However, in general, satisfactory results are obtained when administered at a daily dosage of from about 0.1 mg to about 100 mg, preferably 0.1 to 3 mg, per kg animal body weight, conveniently given in divided doses 2 to 4 times a day, or in sustained release form. For the larger mammals, the total daily dosage is in the range from about 8 to about 150 mg, and dosage forms suitable for oral administration comprise from about 2 mg to about 75 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be in the form of, for example, a solution or a tablet.

In a group of compounds $R_1$ is hydrogen or chlorine, preferably in the 6 or 7 position.

The Example 1 compound is especially interesting in respect of the hypertrophy activity. The Example 3 compound is especially interesting in respect of the antidepressant and anticholinergic utilities.

What is claimed is:

1. A method of treating prostate hypertrophy in animals, which comprises administering to an animal in need of such treatment a therapeutically effective amount of a compound of the formula

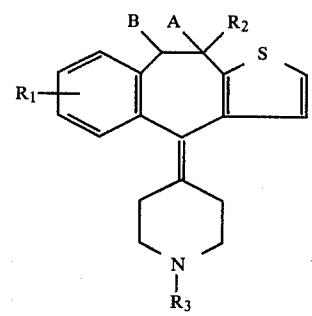

wherein
 $R_1$ is hydrogen, chlorine or lower alkyl,
 $R_2$ is lower alkyl,
 $R_3$ is lower alkyl, each of
 A and B is hydrogen, or
 A and B together form a bond,
or a pharmaceutically acceptable acid addition salt thereof.

2. A method according to claim 1 in which 0.5 to 100 milligrams of the compound are administered daily.

3. A method according to claim 1 in which 0.1 to 50 milligrams of the compound are administered per unit dose.

4. A method according to claim 1 in which the compound is 4-(9,10-dihydro-10-methyl-4H-benzo[4,5]cyclohepta[1,2-b]thiophen-4-ylidene)-1-methylpiperidine.

5. A method according to claim 1 in which the compound is 4-(10-ethyl-9,10-dihydro-4H-benzo[4,5]cyclohepta[1,2-b]thiophen-4-ylidene)-1-methylpiperidine.

* * * * *